(12) United States Patent
Etzkorn

(10) Patent No.: US 10,278,644 B1
(45) Date of Patent: May 7, 2019

(54) METHODS FOR PROVIDING A DYED POLYMER LAYER

(71) Applicant: Verily Life Sciences LLC, Mountain View, CA (US)

(72) Inventor: James Etzkorn, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/636,922

(22) Filed: Jun. 29, 2017

Related U.S. Application Data

(62) Division of application No. 14/189,523, filed on Feb. 25, 2014.

(51) Int. Cl.
*A61B 5/00* (2006.01)
*A61B 5/1468* (2006.01)
*A61B 5/145* (2006.01)

(52) U.S. Cl.
CPC .......... *A61B 5/6821* (2013.01); *A61B 5/0004* (2013.01); *A61B 5/1468* (2013.01); *A61B 5/14532* (2013.01)

(58) Field of Classification Search
CPC .................................................. A61B 5/6821
See application file for complete search history.

(56) References Cited

U.S. PATENT DOCUMENTS

| 6,149,692 A | 11/2000 | Lally et al. | |
|---|---|---|---|
| 7,021,761 B2 | 4/2006 | Kunzler et al. | |
| 7,809,417 B2 | 10/2010 | Abreu | |
| 8,096,654 B2 * | 1/2012 | Amirparviz | B29D 11/00826 345/8 |
| 8,608,310 B2 | 12/2013 | Otis et al. | |
| 8,821,811 B2 * | 9/2014 | Liu | G01N 21/75 422/401 |
| 9,329,410 B2 | 5/2016 | Riall et al. | |
| 9,636,016 B1 * | 5/2017 | Etzkorn | A61B 5/00 |
| 2002/0049389 A1 | 4/2002 | Abreu | |
| 2008/0062381 A1 * | 3/2008 | Doshi | B29D 11/00028 351/159.69 |
| 2010/0113901 A1 * | 5/2010 | Zhang | A61B 5/14532 600/319 |
| 2010/0222657 A1 * | 9/2010 | Ibey | C12Q 1/54 600/316 |
| 2011/0045579 A1 * | 2/2011 | Takahashi | G01N 33/558 435/287.2 |
| 2012/0245444 A1 * | 9/2012 | Otis | A61B 5/1486 600/345 |

(Continued)

FOREIGN PATENT DOCUMENTS

EP 1226465 B1 11/2006

*Primary Examiner* — Cachet I Sellman
(74) *Attorney, Agent, or Firm* — McDonnell Boehnen Hulbert & Berghoff LLP

(57) ABSTRACT

Body-mountable devices comprising a dyed polymer layer that covers a portion of an electronic structure embedded in a transparent polymer are described. An example method for fabricating a body-mountable device includes providing a dyed polymer material on an electronic structure. The electronic structure comprises at least one antenna, a sensor, and an electronic device. The example method also includes molding the dyed polymer material to provide a dyed polymer layer that covers a portion of the electronic structure.

11 Claims, 12 Drawing Sheets

(56) References Cited

U.S. PATENT DOCUMENTS

| | | | | |
|---|---|---|---|---|
| 2012/0259188 A1* | 10/2012 | Besling | .............. | A61B 5/14507 600/319 |
| 2013/0269592 A1* | 10/2013 | Heacock | ............ | A61B 17/3211 116/206 |
| 2014/0268015 A1* | 9/2014 | Riall | ...................... | G02C 7/046 351/158 |
| 2014/0371560 A1* | 12/2014 | Etzkorn | ................. | A61B 5/682 600/365 |
| 2016/0299357 A1* | 10/2016 | Hayashi | ................ | G02C 7/101 |

\* cited by examiner

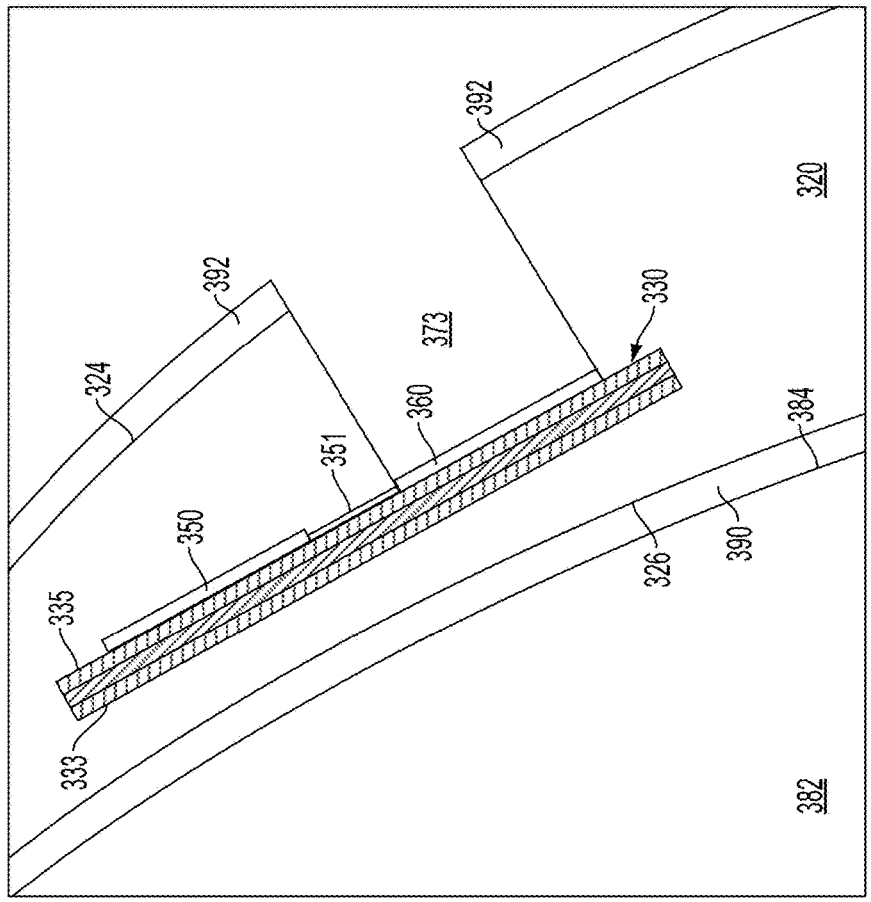
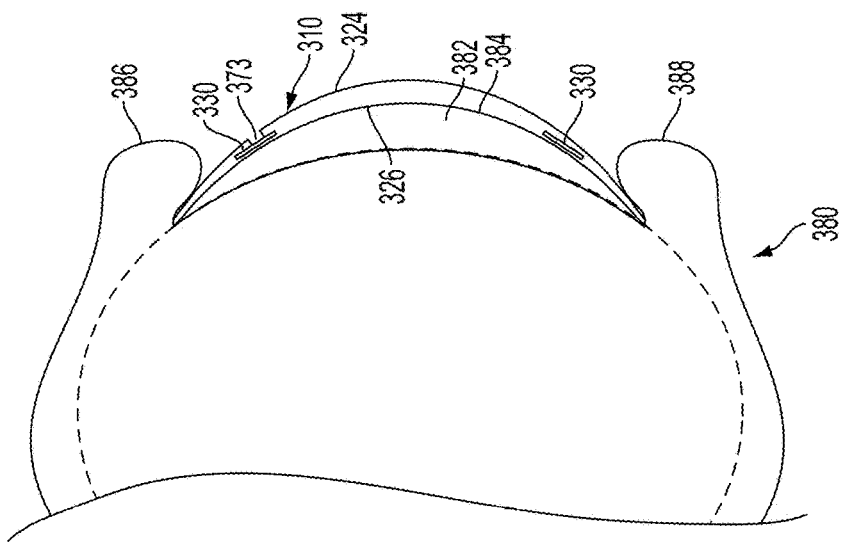
FIG. 3d
FIG. 3c

METHODS FOR PROVIDING A DYED POLYMER LAYER

CROSS-REFERENCE TO RELATED APPLICATIONS

This application is a division of U.S. patent application Ser. No. 14/189,523, filed Feb. 25, 2014, which is incorporated herein by reference.

BACKGROUND

Unless otherwise indicated herein, the materials described in this section are not prior art to the claims in this application and are not admitted to be prior art by inclusion in this section. A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, a method is disclosed. The method includes providing a dyed polymer material on an electronic structure. The electronic structure comprises at least one antenna, a sensor, and an electronic device. The method also includes molding the dyed polymer material to provide a dyed polymer layer that covers a portion of the electronic structure. The dyed polymer layer reduces a visibility of one or more components of the electronic structure included in the portion of the electronic structure.

In another aspect, a device is disclosed. The device includes a transparent polymer. The device also includes an electronic structure comprising at least one antenna, a sensor, and an electronic device. The device further includes a dyed polymer layer that is formed over at least a portion of the electronic structure. The electronic structure and the dyed polymer layer are embedded in the transparent polymer. Additionally, the dyed polymer layer reduces a visibility of one or more components of the electronic structure included in the second portion of the electronic structure.

In yet another aspect, a system is disclosed. The system includes means for providing a dyed polymer material on an electronic structure. The electronic structure comprises at least one antenna, a sensor, and an electronic device. The system also includes means for molding the dyed polymer material to provide a dyed polymer layer that covers a portion of the electronic structure. The dyed polymer layer reduces a visibility of one or more components of the electronic structure included in the portion of the electronic structure.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3c is a side cross-section view of the eye-mountable device shown in FIG. 3a while mounted to a corneal surface of an eye, according to an example embodiment.

FIG. 3d is a side cross-section view showing tear film layers surrounding the surfaces of the eye-mountable device mounted as shown in FIG. 3c, according to an example embodiment.

FIG. 4b is a side view of the eye-mountable device shown in FIG. 4a.

DETAILED DESCRIPTION

Figure 1:
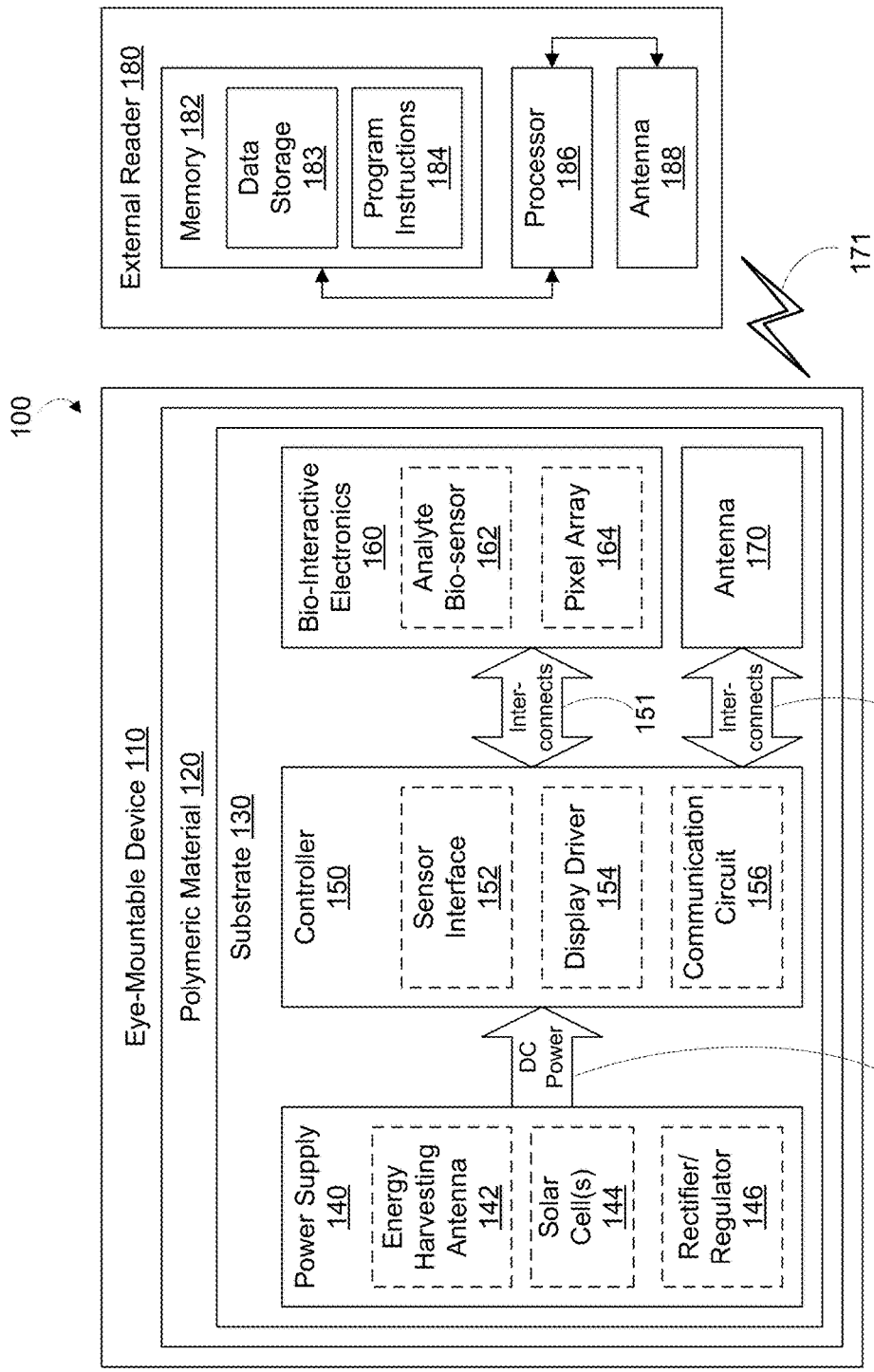
FIG. 1 is a block diagram of a system that includes an eye-mountable device in wireless communication with an external reader, according to an example embodiment.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Introduction

An electronic structure configured for use in a body-mountable device may include at least one antenna, a sensor, and an electronic device. In one example, the body-mountable device is fabricated such that the electronic structure is positioned between an anterior polymer layer and a posterior polymer layer. The polymer layers may be transparent, whereas at least some components of the electronic structure are metallic. For instance, the at least one antenna may comprise one or more layers of gold, platinum, palladium, and/or copper. When the body-mountable device is worn, the metallic components of the electronic structure may be visible. The visibility of the metallic components may be undesirable for some users.

Embodiments described herein relate to body-mountable devices and methods for fabricating body-mountable devices that include a dyed polymer layer. The dyed polymer layer may include a relatively thin, substantially opaque layer of a dyed polymer material that covers an anterior surface of one or more components of the electronic structure. An example method includes providing a dyed polymer material on a first portion of the electronic structure. The method may further comprise molding the dyed polymer material to provide a dyed polymer layer that covers a second portion of the electronic structure. Typically, the second portion of the electronic structure includes a greater area than the first portion of the electronic structure, though this may not be the case in every example.

The dyed polymer layer may "camouflage" a portion of the electronic structure by covering one or more metallic components that would otherwise be visible when the body-mountable device is worn. When the body-mountable device is an eye-mountable device, for example, a color of the dyed polymer material may correspond to an eye color of a user, such as blue, green, hazel, brown, dark brown, or even black. As used herein, the term "eye color" refers to the color of an iris of an eye. The dyed polymer layer may blend with the user's eye color, which may reduce the visibility of the electronic structure and make the make the body-mountable device less apparent to observers of the user wearing the body-mountable device.

II. Example Systems and Devices

A body-mountable device may be configured to monitor health-related information based on at least one analyte detected in a fluid of a user wearing the body-mountable device. An example body-mountable device that comprises an eye-mountable device that is configured to detect the at least one analyte in a tear film of a user wearing the eye-mountable device will now be described in greater detail.

FIG. 1 is a block diagram of a system 100 with an eye-mountable device 110 in wireless communication with an external reader 180, according to an example embodiment. The exposed regions of the eye-mountable device 110 are made of a polymeric material 120 formed to be contact-mounted to a corneal surface of an eye. In accordance with exemplary methods, the polymeric material 120 may comprise a first polymer layer and a second polymer layer.

Substrate 130 is embedded in the polymeric material 120 to provide a mounting surface for a power supply 140, a controller 150, bio-interactive electronics 160, and an antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it may also be referred to as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the anterior or outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more bio-compatible materials, such as those employed for use in contact lenses or other ophthalmic applications involving direct contact with the corneal surface. The polymeric material 120 can optionally be formed in part from such bio-compatible materials or can include an outer coating with such bio-compatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130.

The substrate 130 can be a relatively rigid polymeric material, such as polyethylene terephthalate ("PET"), parylene, or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from a center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in a center region of the eye-mountable device 110. The bio-interactive electronics 160 and/or the substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display driver instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a 1 centimeter diameter, a radial thickness of approximately 1 millimeter, and a thickness of about 50 micrometers. The substrate 130 can optionally be aligned with the curvature of the anterior side of the eye-mountable device 110.

The power supply 140 is configured to harvest ambient energy to power the controller 150 and the bio-interactive electronics 160. For example, a radio-frequency energy harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system (not shown) can be included to capture energy from ambient vibrations. The energy-harvesting antenna 142 can optionally be a dual-purpose antenna that is also used to communicate information to the external reader 180. That is, the functions of the antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the energy harvesting antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices arranged to mitigate high frequency variations in the ambient energy harvesting antenna 142 and/or solar cell(s) 144. For example, an energy storage device (e.g., capacitor, inductor, etc.) can be connected to the output of the rectifier/regulator 146 so as to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as an analyte bio-sensor 162, in bio-interactive electronics 160 to obtain input from the biological environment. Alternatively or additionally, the interaction could involve the use of one or more components, such as the pixel array 164, to provide an output to the biological environment.

In one example, a sensor interface module 152 can be included for operating the analyte bio-sensor 162. The analyte bio-sensor 162 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 152 can be a potentiostat configured to apply a voltage difference between the working and reference electrodes while measuring a current through the working electrode.

In some embodiments, at least a portion of the bio-interactive electronics 160, the controller 150, the power supply, and/or the antenna 170 can be embedded in the substrate 130. And, in some embodiments, at least a portion of the bio-interactive electronics 160 (e.g., the analyte bio-sensor 162) can be surrounded by the substrate 130, except for a surface of the at least a portion of the bio-interactive electronics 160 being exposed by an opening in the substrate 130.

In some instances, a reagent can also be included to sensitize the electrochemical sensor to desired analytes. For example, a layer of glucose oxidase ("GOX") can be situated around the working electrode to catalyze glucose into hydrogen peroxide ($H_2O_2$). The hydrogen peroxide can then be oxidized at the working electrode, which releases electrons to the working electrode, which generates a current.

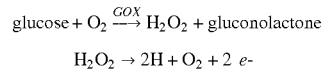

$$glucose + O_2 \xrightarrow{GOX} H_2O_2 + gluconolactone$$
$$H_2O_2 \rightarrow 2H + O_2 + 2\ e\text{-}$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules flow and/or diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the external reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the antenna 170 can be implemented with the same physical antenna. For example, a loop antenna can both harvest incident radiation for power generation and communicate information via backscatter radiation.

The external reader 180 includes an antenna 188 (or group of more than one antenna) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g., RAM) or non-volatile (e.g., ROM) storage system readable by the processor 186. The memory 182 can include a data storage 183 to store indications of data substrates, such as sensor readings (e.g., from the analyte bio-sensor 162), program settings (e.g., to adjust behavior of the eye-mountable device 110 and/or external reader 180), etc. The memory can also include program instructions 184 for execution by the processor 186 to cause the external reader to perform processes specified by the program instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged into a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the substrate of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 647 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162 sufficient to cause the analyte to undergo an electrochemical reaction at the working electrode. The current through the working electrode can be measured to provide the sensor output indicative of the analyte concentration. The controller 150 can operate the antenna 170 to communicate the sensor results back to the external reader 180 (e.g., via the communication circuit 156). The sensor result can be communicated by, for example, modulating an impedance of the antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the on-board controller 150 and the bio-interactive electronics 160. For example, radio frequency radiation 171 can be supplied to power the eye-mountable device 110 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
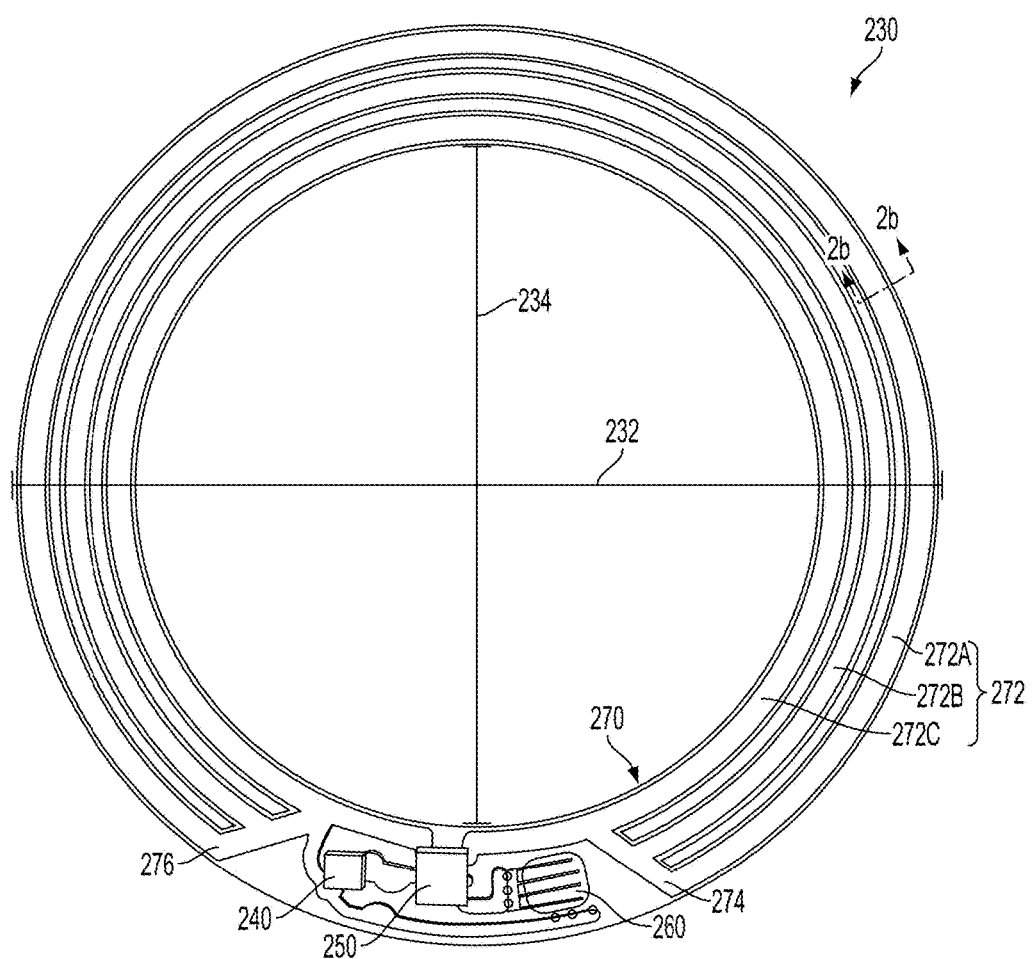
FIG. 2a is a top view of a structure, according to an example embodiment.

FIG. 2A is a top view of an electronic structure 230, according to an example embodiment. In particular, the electronic structure 230 has an outer diameter 232 and an inner diameter 234 and includes electronics 240, electronics 250, a sensor 260, and an antenna 270 disposed thereon. The electronic structure 230 may take the form of or be similar in form to the substrate 130.

The electronic structure 230 can have various sizes. For instance, the size of the electronic structure 230 may depend on which analyte an eye-mountable device is configured to detect. In an example, the electronic structure 230 has a maximum height of approximately 50 between 150 micrometers. Of course, other maximum heights of the electronic structure 230 are possible as well.

In an example, the electronic structure 230 has a height dimension of at least 50 micrometers. In other words, at some point of the electronic structure 230, the height of the electronic structure 230 may be at least 50 micrometers. In an example, this height dimension may correspond to a maximum height of the electronic structure 230. In accordance with the present disclosure, the maximum height of the electronic structure 230 corresponds to the height of the electronic structure 230 at its highest point. For instance, in the example where the electronic structure 230 comprises the sensor 260 and the electronics 250, the height of the electronic structure 230 may vary (and thus the electronic structure 230 may have various height dimensions). For example, the height of the electronic structure 230 may be higher at a point where the electronics 250 is mounted on the electronic structure 230, whereas the height may be lower at a point where there is no chip on the electronic structure 230. In such an example, the maximum height may correspond to the point where the electronics 250 is mounted on the electronic structure 230.

The outer diameter 232 and the inner diameter 234 could take various different forms in various different embodiments. In some embodiments, the outer diameter can have a length between 12.5 and 15 millimeters. Moreover, in some embodiments, the inner diameter can have a length greater than 8 millimeters. And other lengths of the outer diameter 232 and/or inner diameter 234 are possible as well.

The electronics 240 and 250 could be configured in a variety of ways. For example, the electronics 240 and/or the electronics 250 may be configured to operate the sensor 260 and the antenna 270. And, in such an example, the electronics 240 and/or the electronics 250 may be configured for wireless communication with an external reader, such as the external reader 180. In some embodiments, the electronics 240 and the electronics 250 may provide a bias voltage for the sensor 260 and adjust backscattered radio frequency (RF) that is proportional to a current that is passing through the sensor 260.

The electronics 240 and the electronics 250 could take various different forms in various different embodiments. In some embodiments, the electronics 240 and/or the electronics 250 can comprise a chip including one or more logical elements. The electronics 240 and/or the electronics 250 may take the form of or be similar in form to the controller 150.

The sensor 260 is configured to detect one or more analytes. The sensor 260 could take various different forms in various different embodiments. In some embodiments, the sensor 260 can comprise a pair of electrodes, such as a working electrode and a reference electrode. The sensor 260 may take the form of or be similar in form to the analyte bio-sensor 162.

The antenna 270 is configured for communications and/or harvesting energy as described herein. The antenna 270 includes a plurality of conductive loops 272 spaced apart from each other between the outer diameter 232 and the inner diameter 234. In the illustrated example, the plurality of conductive loops 272 includes three conductive loops 272A, 272B, and 272C. However, in other examples, a plurality of conductive loops may include more than three conductive loops, such as five conductive loops, nine conductive loops, etc.

As shown in FIG. 2A, the conductive loops 272A, 272B, and 272C are connected in parallel. With this arrangement, each of the conductive loops in the plurality of conductive loops 272 is electrically connected to the electronics 240, the electronics 250, and the sensor 260 via a first connection 274 and a second connection 276. And the electronics 240, the electronics 250, and the sensor 260 are electrically connected via the first connection 274 and the second connection 276. The first connection 274 and the second connection 276 may take the form of or be similar in form to the interconnects 151 and 157. Moreover, as shown in FIG. 2A, the conductive loops 272A, 272B, and 272C are substantially concentric. The term "substantially concentric," as used in this disclosure, refers to exactly concentric and/or one or more deviations from exactly concentric that do not significantly impact embedding a structure in a body-mountable device as described herein.

And as shown in FIG. 2A, the conductive loops 272A, 272B, and 272C are spaced apart from each other between the outer diameter 232 and the inner diameter 234. In an example, the conductive loops 272A, 272B, and 272C can be spaced apart from adjacent conductive loops by a distance between 100 to 200 micrometers. Other distances are possible as well.

In some embodiments, one of the conductive loops 272A, 272B, and 272C can have a width of 333 micrometers. Other widths of the conductive loops 272A, 272B, and 272C are possible as well. Moreover, in some embodiments, the conductive loops 272A, 272B, and 272C can each have the same width (e.g., the conductive loops 272A, 272B, and 272C can each have a width of 333 micrometers). However, in some embodiments, the conductive loops 272A, 272B, and 272C might not have the same width.

Figure 2B:
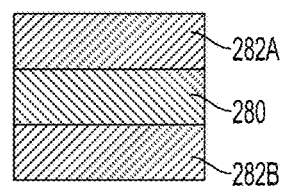
FIG. 2b is a side cross-section view of the structure shown in FIG. 2a, according to an example embodiment.

Each conductive loop in the plurality of conductive loops 272 can comprise a respective metal layer disposed between respective polymer layers. With this arrangement, the polymer layers might block moisture from the metal layer. FIG. 2B is a side cross-section view of the structure shown in FIG. 2A, according to an example embodiment. As shown in FIG. 2B, the conductive loop 272A comprises a metal layer 280 disposed between polymer layers 282A and 282B. The respective metal layers of the conductive loops 272B and 272C may take the form of or be similar in form to the to the metal layer 280, and the respective polymer layers of the conductive loops 272B and 272C may take the form of or be similar in form to the polymer layers 282A and 282B.

In some embodiments, the metal layer 280 can comprise gold or another conductive material that can be deposited on the electronic structure 230, such as platinum, palladium, titanium, carbon, aluminum, copper, silver, and/or silver-chloride. And in at least one such embodiment, the metal layer 280 can have a thickness between 5 and 30 micrometers. Other thicknesses of the metal layer 280 are possible as well. In an example, the metal layer 280 can be formed by a process that includes electroplating.

Moreover, in some embodiments, the polymer layers 282A and 282B can comprise a relatively rigid transparent bio-compatible polymer, such as PET or parylene-C (e.g., dichlorodi-p-xylylene). Each bio-compatible polymer included in the polymer layers 282A and 282B may have an associated glass transition temperature and an associated melting temperature. And in at least such embodiment, the polymer layers 282A and 282B can have a thickness between 10 and 50 micrometers, such as 15 micrometers. Other thicknesses of the polymer layers 282A and 282B are possible as well. In an example, the polymer layers 282A and 282B can be formed by a process that includes chemical vapor deposition.

In an example, the plurality of conductive loops 272 can be formed by a process that includes etching a portion of a metal layer disposed between polymer layers with an inductively coupled plasma, such as an oxygen plasma.

Figure 3A:
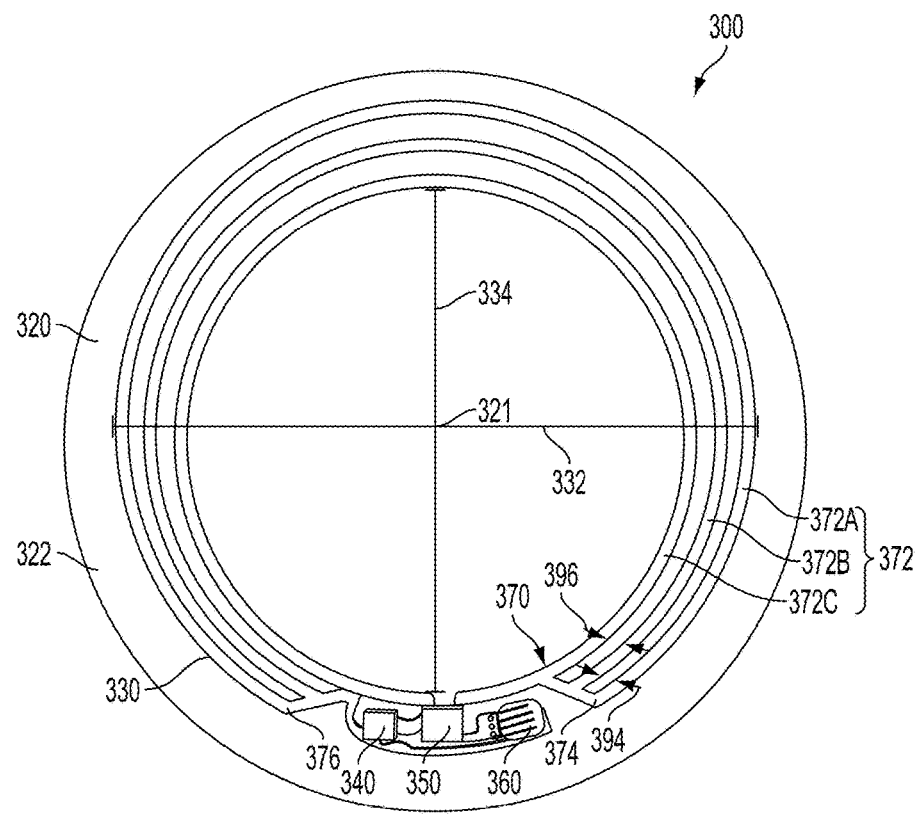
FIG. 3a is a top view of an eye-mountable device, according to an example embodiment.
Figure 3B:
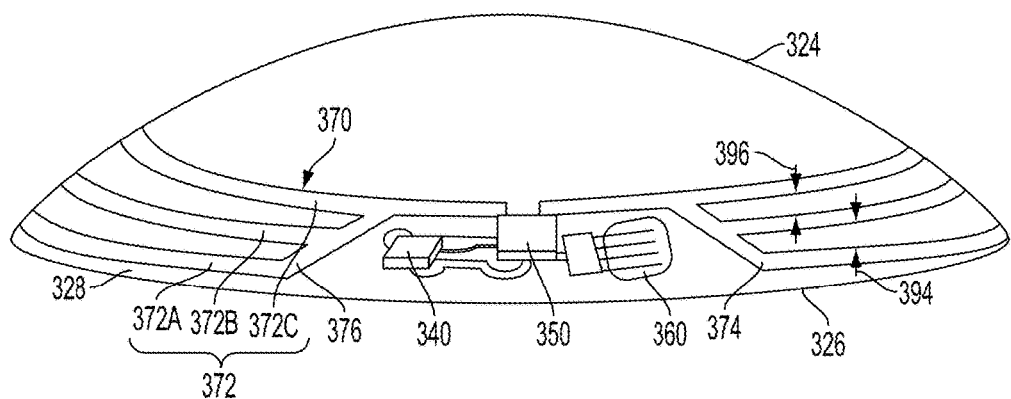
FIG. 3b is a side view of the eye-mountable device shown in FIG. 3a, according to an example embodiment.

FIG. 3a is a top view of an eye-mountable device 300. FIG. 3b is a side view of the eye-mountable device 300 shown in FIG. 3a. It is noted that relative dimensions in FIGS. 3a and 3b are not necessarily to scale, but have been rendered for purposes of explanation only in describing the arrangement of the eye-mountable electronic device 300. The eye-mountable device 300 is formed of a transparent polymer 320 shaped as a curved disk. The transparent polymer 320 can be a substantially transparent material to allow incident light to be transmitted to the eye while the eye-mountable device 300 is mounted to the eye. The transparent polymer 320 can be a bio-compatible material similar to those employed to form vision correction and/or cosmetic contact lenses in optometry, such as PET, polymethyl methacrylate ("PMMA"), silicone hydrogels, combinations of these, etc. The transparent polymer 320 could take the form of or be similar in form to the polymeric material 120.

The transparent polymer 320 can be formed with one side having a posterior side 326 (i.e., concave surface) suitable to fit over a corneal surface of an eye. The opposing side of the disk can have an anterior side 324 (i.e., convex surface) that does not interfere with eyelid motion while the eye-mountable device 300 is mounted to the eye. A circular outer side edge 328 connects the posterior side 326 and anterior side 324.

The eye-mountable device 300 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 300 can be selected according to the size and/or shape of the corneal surface and/or the scleral surface of the wearer's eye.

While the eye-mountable device 300 is mounted in an eye, the anterior side 324 faces outward to the ambient environment while the posterior side 326 faces inward, toward the corneal surface. The anterior side 324 can therefore be considered an outer, top surface of the eye-mountable device 300 whereas the posterior side 326 can be considered an inner, bottom surface. The "top" view shown in FIG. 3a is facing the anterior side 324.

The electronic structure 330 is embedded in the transparent polymer 320. The substrate 330 can be embedded to be situated along an outer periphery 322 of the transparent polymer 320, away from a center region 321. The electronic structure 330 does not interfere with vision because it is too close to the eye to be in focus and is positioned away from the center region 321 where incident light is transmitted to the light-sensing portions of the eye. The electronic structure 330 can take the form or be similar in form to the substrate 130 and/or the electronic structure 230.

The electronic structure 330 has an outer diameter 332 and an inner diameter 334 and includes electronics 340, electronics 350, a sensor 360, and an antenna 370 disposed thereon. The outer diameter 332 may take the form of or be similar in form to the outer diameter 232, the inner diameter 334 may take the form of or be similar in form to the inner diameter 234, the electronics 340 may take the form of or be similar in form to the controller 150 and/or the electronics 240, the electronics 350 may take the form or be similar in form to the controller 150 and/or the electronics 250, and the sensor 360 may take the form or be similar in form to the bio-analyte sensor 162 and/or the sensor 260.

The antenna 370 is configured for communications and/or harvesting energy, like the antenna 270 is configured for communications and/or harvesting energy. The antenna 370 includes a plurality of conductive loops 372 spaced apart from each other between the outer diameter 332 and the inner diameter 334. In the illustrated example, the plurality of conductive loops 372 includes three conductive loops 372A, 372B, and 372C. However, in other examples, a plurality of conductive loops may include more than three conductive loops, such as five conductive loops, nine conductive loops, etc. When the electronic structure 330 is embedded in the transparent polymer 320, the conductive loops 372A, 372B, and 372C may move relative to each other.

The conductive loops 372A, 372B, and 372C can have an arrangement similar to an arrangement of the conductive loops 272A, 272B, and 272C. As shown in FIGS. 3a and 3b, the conductive loops 372A, 372B, and 272C are connected in parallel. With this arrangement, each of the conductive loops in the plurality of conductive loops 372 is electrically connected to the electronics 340, the electronics 350, and the sensor 360 via a first connection 374 and a second connection 376. And the electronics 340, the electronics 350, and the sensor 360 are electrically connected via the first connection 374 and the second connection 376. The first connection 374 and the second connection 376 may take the form of or be similar in form to the first connection 274 and the second connection 276 and/or the interconnects 151 and 157. Moreover, as shown in FIGS. 3a and 3b, the conductive loops 372A, 372B, and 372C are substantially concentric. And as shown in FIGS. 3a and 3b, the conductive loops 372A, 372B, and 372C are spaced apart from each other between the outer diameter 332 and the inner diameter 334.

The conductive loops 372A, 372B, and 372C may have a width that is the same or similar to a width of the conductive loops 272A, 272B, and 272C. Moreover, each of the conductive loops in the plurality of conductive loops 372 can comprise a respective metal layer disposed between respective polymer layers, like the conductive loops in the plurality of conductive loops 272 comprise a respective metal layer disposed between respective polymer layers. And the plurality of conductive loops 372 can be formed like the plurality of conductive loops 272 is formed.

In the illustrated example, the metal and polymer layers in each conductive loop in the plurality of conductive loops 372 are spaced apart from the metal and polymer layers in each adjacent conductive loop in the in the plurality of conductive loops 372. In some embodiments, the transparent polymer 320 can extend between adjacent conductive loops (e.g., the conductive loop 372A and the conductive loop 372B and/or the conductive loop 372B and the conductive loop 372C) in the plurality of conductive loops 372.

Moreover, in the illustrated example, the metal and polymer layers of conductive loop 372B are spaced apart from the metal and polymer layers of adjacent conductive loop 372A by a first distance 394, and the metal and polymer layers of conductive loop 372B are spaced apart from the metal and polymer layers of adjacent conductive loop 372C by a second distance 396. In an example, the first distance 394 and the second distance 396 can be between 100 to 200 micrometers. Other distances are possible as well.

The first distance 394 could be a different value than the second distance 396. In some embodiments, the first distance 394 can be greater (or less) than the second distance 396. And the first distance 394 and/or the second distance 396 could vary. In some embodiments, the first distance 394 can vary based on a rotational orientation of the conductive loop 372B relative to the conductive loop 372A and/or the conductive loop 372C. Moreover, in some embodiments, the second distance 396 can vary based on a rotational orientation of the conductive loop 372B relative to the conductive loop 372C and/or the conductive loop 372A.

FIG. 3c is a side cross-section view of the eye-mountable 310 while mounted to a corneal surface 384 of an eye 380, according to an example embodiment. FIG. 3d is a close-in side cross-section view enhanced to show tear film layers 390, 392 surrounding exposed surfaces 324, 326 of the eye-mountable device 300, according to an example embodiment. It is noted that relative dimensions in FIGS. 3c and 3d are not necessarily to scale, but have been rendered for purposes of explanation only in describing the arrangement of the eye-mountable electronic device 300. For example, the total thickness of the eye-mountable device 300 can be about 200 micrometers, while the thickness of the tear film layers 390, 392 can each be about 10 micrometers, although this ratio may not be reflected in the drawings. Some aspects are exaggerated to allow for illustration and facilitate explanation.

The eye 380 includes a cornea 382 that is covered by bringing the upper eyelid 386 and lower eyelid 388 together over the top of the eye 380. Incident light is received by the eye 380 through the cornea 382, where light is optically directed to light-sensing elements of the eye 380 (e.g., rods and cones, etc.) to stimulate visual perception. The motion of the eyelids 386, 388 distributes a tear film across the exposed corneal surface 384 of the eye 380. The tear film is an aqueous solution secreted by the lacrimal gland to protect and lubricate the eye 380. When the eye-mountable device 300 is mounted in the eye 380, the tear film coats both the anterior and posterior sides 324, 326 with an inner layer 390 (along the posterior side 326) and an outer layer 392 (along the anterior side 324). The tear film layers 390, 392 can be about 10 micrometers in thickness and together account for about 10 microliters.

The tear film layers 390, 392 are distributed across the corneal surface 384 and/or the posterior side 324 by motion of the eyelids 386, 388. For example, the eyelids 386, 388 raise and lower, respectively, to spread a small volume of tear film across the corneal surface 384 and/or the anterior side 324 of the eye-mountable device 300. The tear film layer 390 on the corneal surface 384 also facilitates mounting the eye-mountable device 300 by capillary forces between the anterior side 326 and the corneal surface 384. In some embodiments, the eye-mountable device 300 can also be held over the eye in part by vacuum forces against the corneal surface 384 due to the concave curvature of the eye-facing anterior side 326.

In some embodiments, a polymer layer defining the anterior side 326 may be greater than 50 micrometers thick, whereas a polymer layer defining the posterior side 324 may be less than 150 micrometers. Thus, when the sensor 360 is mounted on an outward-facing surface 335 (as shown in FIG. 3d) the sensor 360 may be at least 50 micrometers away from the anterior side 324 and may be a greater distance away from the posterior side 326. However, in other examples, the sensor 360 may be mounted on an inward-facing surface 333 of the electronic structure 330 such that the sensor 360 is facing the posterior side 326. The sensor 360 could also be positioned closer to the anterior side 324 than the posterior side 326. With this arrangement, the sensor 360 can receive analyte concentrations in the tear film 392 via a channel 373. In some examples, analyte concentrations in the tear film 390 and/or 392 may diffuse through the transparent polymer 320 to the sensor 360. As a result, the eye-mountable device 300 might not include the channel 373.

Figure 4A:
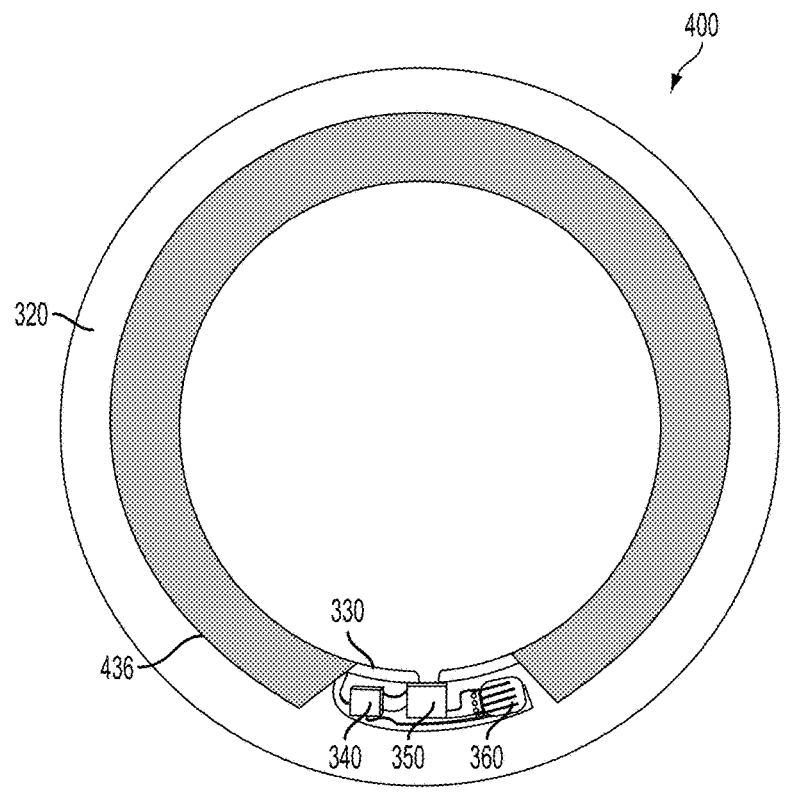
FIG. 4a is a top view of another eye-mountable device, according to an example embodiment.
Figure 4B:
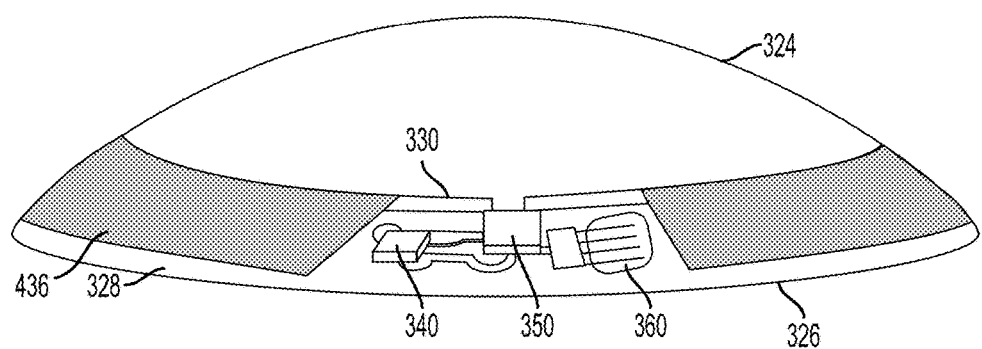

FIG. 4a is a top view of an eye-mountable device 400. FIG. 4b is a side view of the eye-mountable device 400 shown in FIG. 4A. As with FIGS. 3a and 3b, it is noted that relative dimensions in FIGS. 4a and 4b are not necessarily to scale, but have been rendered for purposes of explanation only in describing the arrangement of the eye-mountable device 300. The components of the eye-mountable device 400 are the same as or are substantially similar to the components of the eye-mountable device 300 described with respect to FIGS. 3a-3d.

The eye-mountable device 400 also includes a dyed polymer layer 436. A color of the dyed polymer layer 436 may be the same as or substantially similar to the user's eye color. In this manner, the dyed polymer layer 436 may camouflage (i.e., hide or obscure) an anterior surface of one or more components of the electronic structure 330 that would otherwise be visible from the anterior side 324 of the eye-mountable device 400. That is, the color of the dyed polymer layer 436 may blend with the user's eye color, thereby reducing the visibility of the components of the electronic structure and making the eye-mountable device less apparent to observers of the user wearing the eye-mountable device.

In the example illustrated in FIGS. 4a and 4b, for instance, the dyed polymer layer 436 covers substantially all of an anterior surface of the antenna 370. As previously noted, the antenna 370 may include a plurality of conductive loops 372, each of which may comprise one or more conductive, metallic materials, such as, for example, gold. The dyed polymer layer 436 may limit the visibility of the anterior surfaces of each conductive loop in the plurality of conductive loops 372.

In another example, the dyed polymer layer 436 may cover additional components of the electronic structure 330. For instance, the dyed polymer layer 436 may anterior surfaces of the electronic devices 340 and 350. Depending on the application and type of analysis performed by the electronic structure 330, the dyed polymer layer 436 may also or additionally cover the sensor 360. And in yet another example, the dyed polymer layer 436 may cover less than substantially all anterior surfaces of the antenna 470.

The dyed polymer layer 436 may comprise a dyed polymer material. The dyed polymer material may include a polymer material that is the same as or is substantially similar to the polymer material of the transparent polymer 320. The dyed polymer may be prepared by mixing the polymer material with a dye suitable for providing the desired color for the dyed polymer layer 436. The amount of dye used may depend on the color of the dye, the polymer material, and/or a desired amount of transparency of the dyed polymer layer 436. While preferably opaque, the dyed polymer layer 436 could be opaque in some examples and could be partially transparent in other examples.

In one example, the color of the dyed polymer layer 436 is one of blue, green, hazel, brown, dark brown, or even black (e.g., to match the color of the iris of a user who would be wearing the device). In another example, the dyed polymer layer 436 is a shade of one of these colors. Moreover, the color of the dyed polymer layer 436 may be customized to match the user's specific eye color. And in yet other examples, the color of the dyed polymer layer 436 may include one or more other colors. For instance, the user may want to increase the noticeability of the eye-mountable device 400, perhaps by choosing a color of the dyed polymer layer that contrasts the user's eye color. As one example, if the user's eye color is blue, the user may choose a shade of red as color of the dyed polymer layer 436 may be red. Other example scenarios are possible as well.

Additionally or alternatively, the dyed polymer layer 436 may comprise two or more colors. For instance, the dyed polymer 436 may have a pattern that reduces the conspicuousness of the eye-mountable device 400. The pattern may comprise two or more shades of a color or, perhaps, of multiple colors. The two or more shade may appear as random spots or blobs in the dyed polymer layer 436, such that the dyed polymer layer 436 approximates the natural variation in color of the iris. In one example, the variation of colors (e.g., the two or more shades) of the dyed polymer layer 436 are based on the variation of a specific user's iris.

While the body-mountable device has been described as comprising the eye-mountable device 110, the eye-mountable device 300, and/or the eye-mountable device 400, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110, the eye-mountable device 300 and/or the eye-mountable device 400. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device. In this example, a different color may be used for a dyed polymer layer similar to the dyed polymer layer 436, such as, for instance, white.

Moreover, in some embodiments, the body-mountable device may comprise a skin-mountable device. In some embodiments, the skin-mountable device may take the form of or be similar in form to the eye-mountable device 110, the eye-mountable device 300 and/or the eye-mountable device 400. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Methods

Providing the dyed polymer layer 436 over a portion of the electronic structure 330 may be incorporated into a process for fabricating the eye-mountable device 400. FIGS. 5a-l illustrate stages in a fabricating a body-mountable device, such as the eye-mountable device 400 shown in FIGS. 4a and 4b. While the process described with respect to FIGS. 5a-5l is directed toward fabricating of an eye-mountable device, it is understood that the process may be adapted to fabricate a different body-mountable device.

Moreover, while components of the electronic structure 230 and the eye-mountable devices 300 and 400 described with respect to FIGS. 2a-4b, it is understood that other device and/or components can be used as well.

Figure 5A:
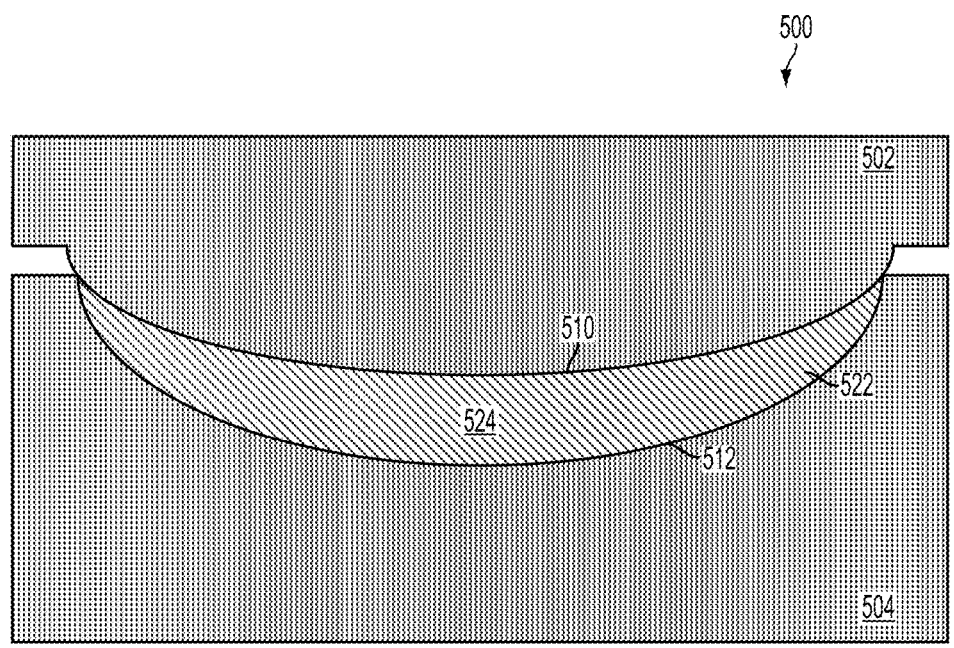
FIG. 5a-l show stages for molding a body-mountable device, according to an example embodiment.

FIG. 5a shows a cross-sectional view of a fabrication device 500 that includes example molding pieces that may be used to form a first polymer layer. In particular, FIG. 5a illustrates a fabrication device 500 including a first molding piece 502 and a second molding piece 504. The first molding piece 502 and the second molding piece 504 may define a first cavity. The second molding piece 504 may be filled with a polymer material 522, and the polymer material 522 may be compressed into a first polymer layer 524 by the first molding piece 502 and/or the second molding piece 504.

After the polymer material 522 is compressed into the first polymer layer 524, the fabrication device 500 may cure the first polymer layer 508. Curing involves the hardening of a polymer material by cross-linking of polymer chains, and curing may be, for example, brought about by chemical additives, ultraviolet radiation, an electron beam, and/or heat. In an example, the polymer material 522 can be a light-curable polymer material, and the fabrication device 500 may be configured to cure the light-curable polymer material using light, such as ultraviolet light or visible light.

In one example, the first polymer layer 520 may be cured to a partially-cured state. This may involve curing the material to a partially-cured state that is, for instance, approximately 50-75% of a fully cured state. Other partially-cured states are possible as well. Beneficially, by partially curing the first polymer layer 524 to a partially-cured state, the first polymer layer 524 may have a tackiness that facilitates adhesion thereto. With this arrangement, the tackiness may ensure that a structure conformed to a curvature of the first polymer layer 524 remains securely fixed in a given location during subsequent formation steps.

The tackiness exhibited by the partially-cured first polymer layer 524 may be different for different polymers. Accordingly, the fabrication device 500 may be configured to cure different polymer materials differently than other polymer materials (e.g., a first polymer material may be cured more than a second polymer material). Further, in addition to light curing, other methods of curing are possible as well, such as chemical additives and/or heat. Yet still further, in other example embodiments, the first polymer layer may be completely cured. Alternatively, the fabrication device may bypass the curing process at this stage.

The first molding piece 502 and the second molding piece 504 may be configured to achieve a given desired thickness of the first polymer layer 524. For instance, in one example, the first polymer layer 524 may have a thickness of less than 150 micrometers. In an example embodiment, the first molding piece 502 and the second molding piece 504 can be designed so as to allow for a polymer layer having a thickness that is less than 150 micrometers. As such, when the first molding piece 502 and the second molding piece 504 are pressed together during the formation of the first polymer layer 524, the resulting first polymer layer 524 will have a thickness of less than 150 micrometers.

In another example, the thickness of the first polymer layer 524 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

The polymer material 522 can be any material that can form an eye-compatible polymer layer. In one example, the polymer material 522 may be a formulation containing polymerizable monomers, such as hydrogels, silicone hydrogels, silicone elastomers, and rigid gas permeable materials. Further, the polymer material 522 may form a transparent or substantially transparent polymer layer. As such, the use of the polymer material 522 may result in an eye-mountable device through which the wearer can see when mounted on the wearer's eye. In one example, the polymer material 522 can be a hydrogel material, such as silicone hydrogel. As known in the art, hydrogel materials are commonly used in contact-lens technology and are well-suited for eye-mountable devices. Other materials are possible as well.

In one example, the first molding piece 502 and/or the second molding piece 504 can be configured so as to allow sufficient pinch off to provide for suitable edges for an eye-mountable device.

The first polymer layer 524 defines a posterior side 510 of an eye-mountable device. That is, the first polymer layer 524 may define an outer edge of the eye-mountable device. When mounted on an eye of a user, the posterior side 510 of the eye-mountable device defined by the first polymer layer 524 corresponds to a side of the device touching the eye of the user. The first molding piece 502 may be shaped so as to define a shape of the posterior side 510. For example, a curvature of the posterior side 510 may be defined by the first molding piece 502. The second molding piece 504 may be shaped so as to define a shape of an upper surface 512 of the first polymer layer 524, such as, for example, a curvature of the upper surface 512. In one example, a structure can be conformed to the curvature of the upper surface 512.

Figure 5B:
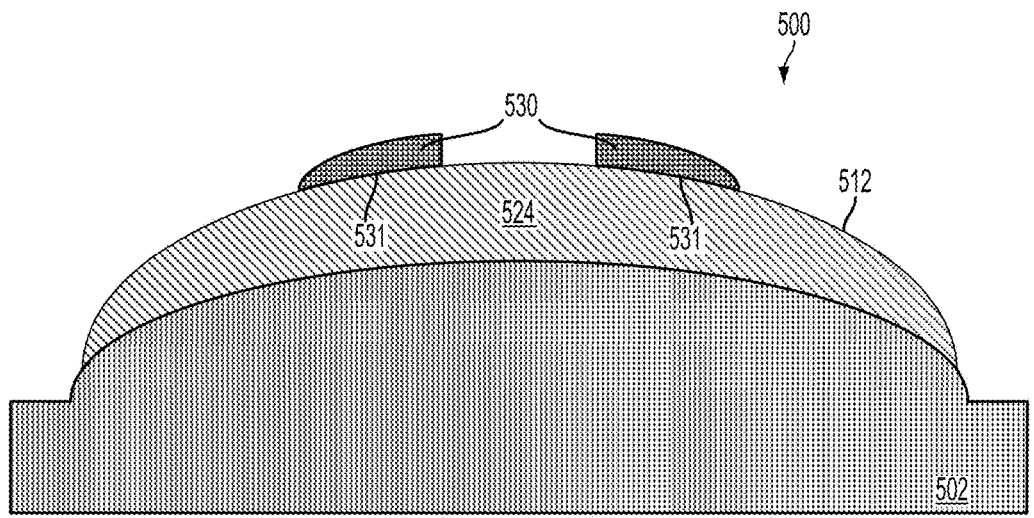

FIG. 5b shows a cross-sectional view of the fabrication device 500 in which an electronic structure 530 is adhered to the upper surface 512. The electronic structure 530 may be the same as or substantially similar to any one of the electronic structures 230 or 330. While the electronic structure 530 is depicted as a solid object in FIGS. 5b-5l, it is to be understood that there may be a space between one or more components of the electronic structure 530 in a cross-sectional view similar to the cross-sectional view shown in FIG. 5b.

The fabrication device 500 may be further configured to position the electronic structure 530 on the upper surface 512. In one example, the fabrication device 500 may employ one or more additional structures (not shown) to position the electronic structure 530. In another example, the fabrication device 500 may comprise a robotic system (not shown) configured to align the electronic structure 530 on the upper surface 512. The robotic system may, for example, use one or more visual cues to align the electronic structure 530 in the proper position on or over the upper surface 512. Other examples are also possible.

Various techniques may be employed to adhere the electronic structure 530 to the upper surface 512. In one example, the fabrication device 500 may be configured to apply an adhesive to a posterior side 531 of the electronic structure 530. In another example, the fabrication device 500 may be configured to adhere the electronic structure 530 to the upper surface 512 when the first polymer layer 524 is in a partially cured state. In this example, the fabrication device 500 may be configured to complete curing of the first polymer layer 524 after the electronic structure 530 has been positioned on the upper surface 512. Other examples are also possible.

Adhering the electronic structure 530 to the first polymer layer 524 may impart a curvature on the electronic structure 530. In one example, the electronic structure 530 may be fabricated on a substantially flat substrate, and may thus be substantially flat when released from the substrate. After the electronic structure 530 is adhered to the upper surface 512 of the first polymer layer 524, the electronic structure 530 may have a curvature that is the same as or substantially similar to the curvature of the upper surface 512. In other examples, the electronic structure 530 may be molded or fabricated to have a curvatures that is the same as or substantially similar to the curvature of the upper surface 512 prior to being adhered to the first polymer layer 524. Other examples may also be possible.

Figure 5C:
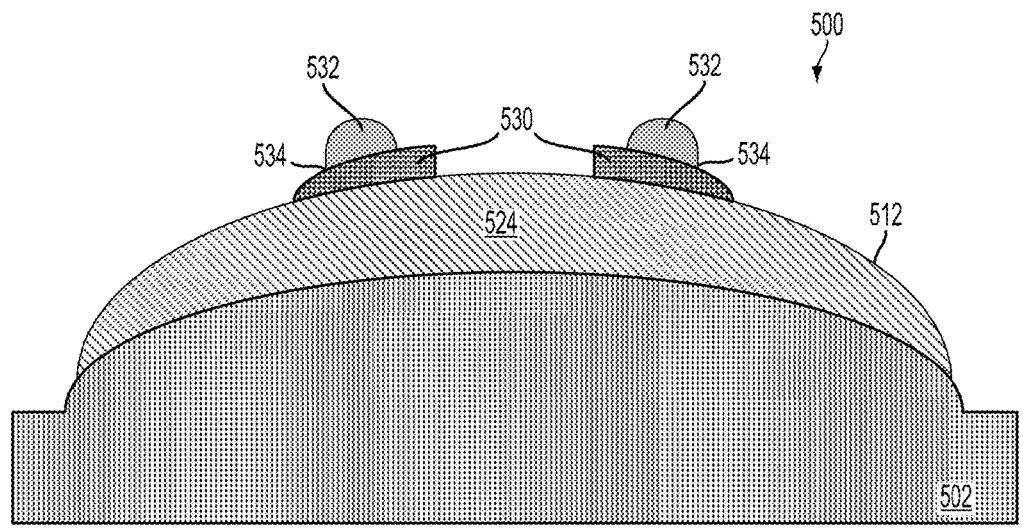

FIG. 5c shows a cross-sectional view of the fabrication device 500 in which a dyed polymer material 532 is provided on a first portion 534 of an anterior surface of the electronic structure 530. In an example in which the electronic structure 530 comprises at least one antenna, such as at least one of the antennas 270 or 370, the first portion 534 may comprise a portion of a surface of the at least one antenna, such as an anterior surface of the at least one antenna.

In another example, the first portion 534 may include portions of additional components of the electronic structure 530. For instance, if the electronic structure 530 further comprises an electronic device, such as one of the electronic devices 240, 250, 340, and/or 350, the first portion 534 may include one or more surfaces of the electronic device.

To promote proper adhesion during the fabrication process, the dyed polymer material 532 may comprise a polymer material that is the same as or is substantially similar to the polymer material 522 used to form the first polymer layer 524 (as described with respect to FIG. 5a) and/or the polymer material 526 used to form the second polymer layer 528 (as described below with respect to FIG. 5j). In an example in which the polymer material 522 comprises silicone, the dyed polymer material 532 may also comprise silicone. For instance, if the polymer material 522 is silicone hydrogel, the dyed polymer material 532 may also be silicone hydrogel.

The fabrication device 500 may provide the dyed polymer material 532 on the first portion of the anterior surface 532 using any number of techniques. For instance, the fabrication device 500 may include a robotic system (not shown) configured to deposit or otherwise provide the dyed polymer material 532 on the first portion 534. Other examples may also be possible.

Figure 5D:
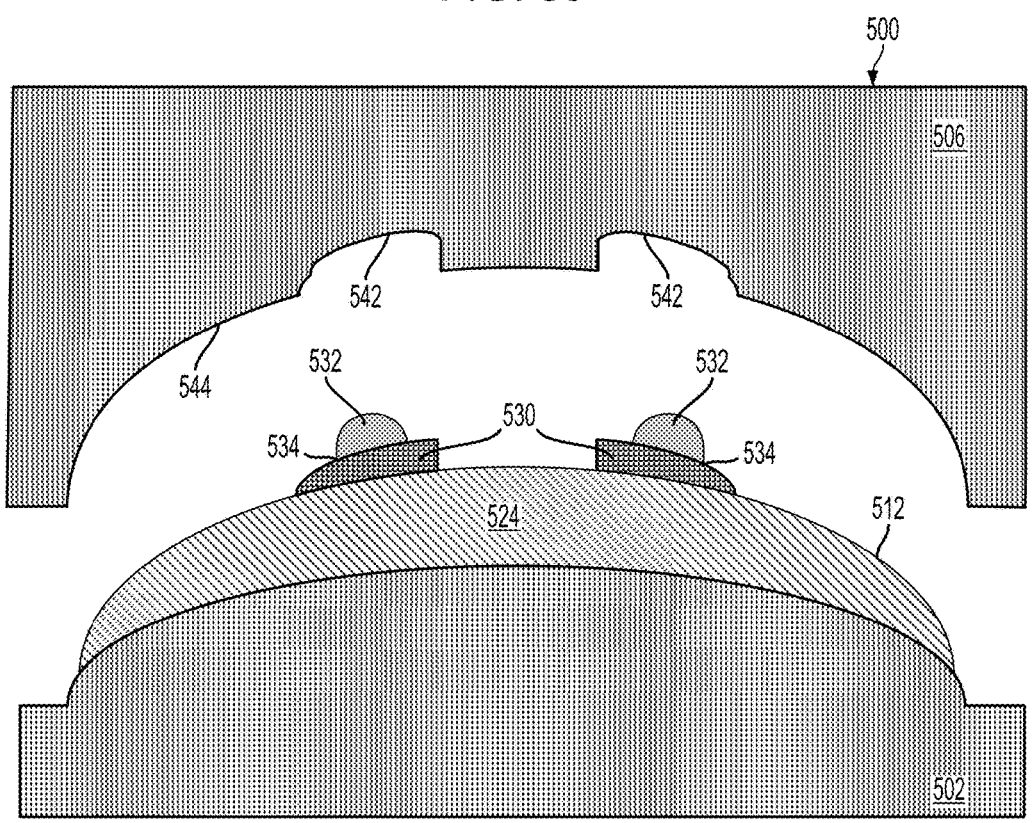

FIG. 5d shows a cross-sectional view of the fabrication device 500 in which a third molding piece 506 is aligned over the first molding piece 502. The third molding piece 506 may include a mold cavity 542 and an inner surface 544. The fabrication device 500 may align the third molding piece 506 over the first molding piece 502 such that the mold cavity 542 is positioned over the electronic structure 530.

The mold cavity 542 may have a shape that is the same as or substantially similar to a shape of the electronic structure 530. For example, if the electronic structure 530 is one of the electronic structures 230 or 330 described in FIGS. 2a-2b and 3a-3d, respectively, the electronic structure 530 may have a ring shape. In this example, the mold cavity 542 may also have a ring shape. In an example in which the electronic structure 530 is configured for use in a body-mountable device other than an eye-mountable device, the electronic structure 530 may have a different shape. In this example, the mold cavity 542 may have a shape that is the same as or substantially similar to a portion of the electronic structure 530 (e.g., a portion of the electronic structure 530 that would be visible when a body-mountable device that includes the electronic structure 530 is worn by a user). Other examples are also possible.

A depth of the mold cavity 542 may depend on a desired thickness of the dyed polymer layer. In one example, the desired thickness of the mold cavity is between about 10 micrometers and about 100 micrometers. Other examples may be possible as well.

Moreover, different portions of the mold cavity 542 may have different depths. For instance, a first portion of the mold cavity 542 may have a first depth, and a second portion of the mold cavity 542 may have a second depth. The first depth may correspond to a desired thickness of the dyed polymer layer. The second depth may be slightly greater than a thickness or a height of one or more components of the electronic structure 530 that will not be covered by the dyed polymer layer. In this manner, the second portion of the mold cavity 542 certain components of the electronic structure 530, such as a sensor, from being covered with the dyed polymer material 532 during subsequent molding steps.

Additionally, the second portion of the mold cavity 542 may include a cutout configured to receive a component that has a thickness or a height greater than the rest of the electronic structure 530. For example, a component of the electronic structure 530, such as an electronic device, may have a thickness or height that is greater than other components, such as the at least one antenna, of the electronic structure 530. If the electronic device is not to be covered by the dyed polymer material 532, the cutout of the mold cavity 542 may have a shape configured to receive the electronic device.

The inner surface 544 of the third molding piece 506 may have a shape that mirrors the shape of the upper surface 512. As shown in FIG. 5d, for instance, the inner surface 544 may have a concave curvature that is substantially similar to, or perhaps even slightly less than, a convex curvature of the upper surface 512. In this manner, the inner surface 544 may minimize the potential for, and may preferably prevent, the upper mold 540 from damaging the first polymer layer 524 when forming the dyed polymer layer. In other examples, the inner surface 544 may have a different shape.

The fabrication device 500 may align the third molding piece 506 over the first molding piece 502 so as to position the mold cavity 542 substantially over the electronic structure 530. In one example, the fabrication device 500 may include one or more alignment pins (not shown), such as one or more dowel pins, for aligning the third molding piece 506. Additionally or alternatively, the fabrication device 500 may include one or more other components or structures for mechanically aligning the third molding piece 506. In another example, the fabrication device 500 includes a robotic system (not shown) configured to align the third molding piece 506 over the first molding piece 502. In an additional or alternative example, the fabrication device 500 may include one or more additional components to align the third molding piece 506 over the first molding piece 502, such as, for instance, a visual alignment system. Other examples may also be possible.

The fabrication device 500 may also align the third molding piece 506 over the first molding piece 502 such that the second portion of the mold cavity 542 is positioned over the components of the electronic structure 530 that will not be covered by the dyed polymer layer. Additionally, if the mold cavity 542 includes a cutout configured to receive an electronic device, the fabrication device 500 may align the third molding piece 506 over the first molding piece 502 such that the cutout is positioned over the electronic device.

Figure 5E:
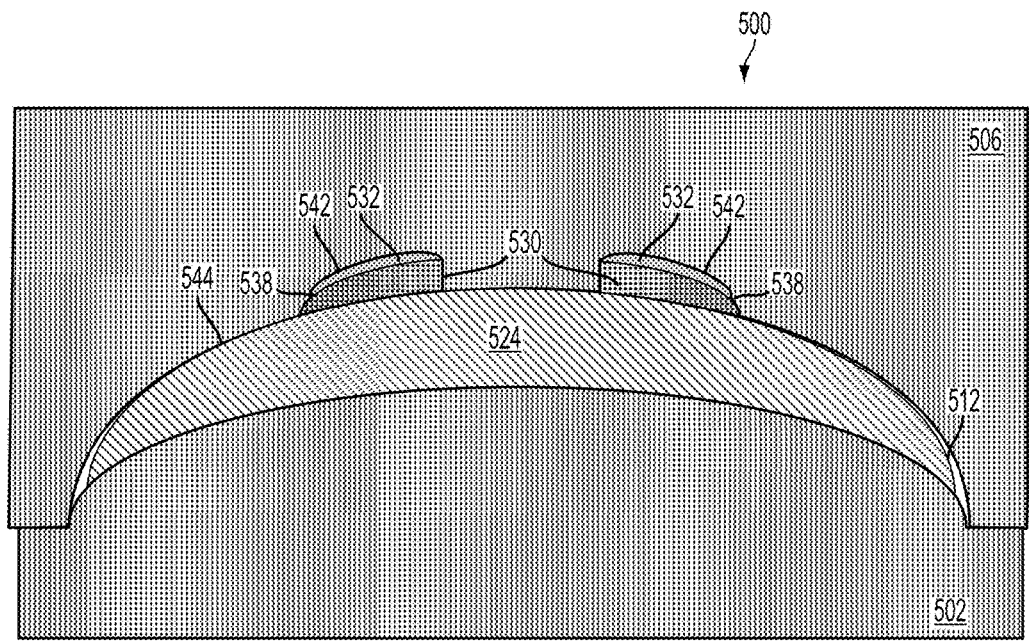

After the fabrication device 500 aligns the third molding piece 506 over the first molding piece 502, the fabrication device 500 may use the third molding piece 506 to compress the dyed polymer material 532, as shown in FIG. 5e. Compressing the dyed polymer material 532 may cause the dyed polymer material 532 to fill the mold cavity 544, thereby causing the dyed polymer material 532 to cover a second portion 538 of the anterior surface of the electronic structure 530.

The second portion 538 may include a surface area of the anterior surface of the electronic structure 530 that is greater than or equal to a surface area of the first portion 534. For instance, if the first portion 534 includes a portion of the anterior surface of the at least one antenna of the electronic structure 530, the second portion 538 may include substantially all of the anterior surface of the at least one antenna. Moreover, in some examples the second portion 538 may include substantially all of the anterior surface of the electronic structure 530. Other examples may also be possible.

After compressing the dyed polymer material 532, the fabrication device 500 may cure the dyed polymer material 532. The fabrication device 500 may cure the dyed polymer material 532 using the same or a substantially similar technique as used to cure the first polymer layer 524. Alternatively, the fabrication device 500 may cure the dyed polymer material 532 using any curing technique suitable for the materials of the dyed polymer material 532, the electronic structure 530, and first polymer layer 524.

Figure 5F:
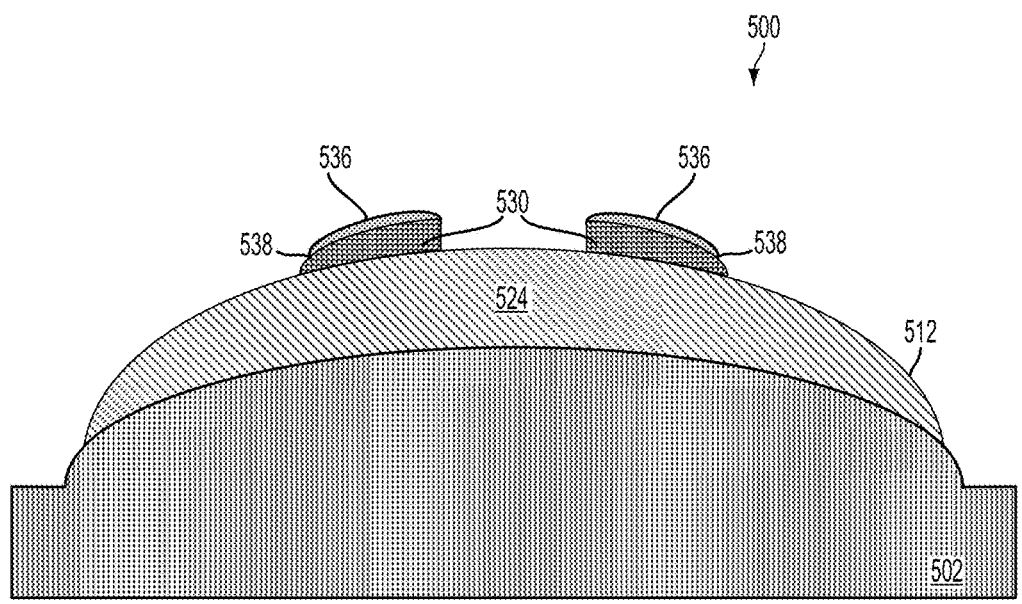

Once the dyed polymer material 532 is cured, the fabrication device 500 may remove the third molding piece 506. The third molding piece 506 may include a pinch off along each of the inner edge and outer edge of the mold cavity 542 to provide for a dyed polymer layer 536 with suitable edges. As shown in FIG. 5f, the dyed polymer layer 536 may cover the second portion 538 of the electronic structure 530.

Figure 5G:
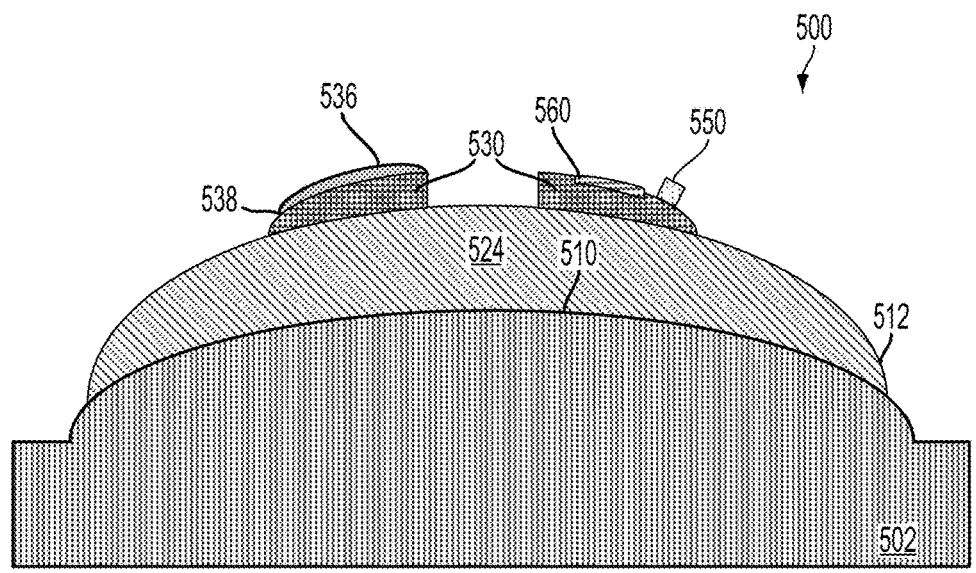

In some examples, the dyed polymer layer 536 may not cover some components of the electronic structure 530. FIG. 5g is a rotated view of FIG. 5f. In the example illustrated in FIG. 5g, for instance, the dyed polymer layer 536 does not cover an electronic device 550 and a sensor 560. The electronic device 550 may be the same as or substantially similar to any one of the electronic devices 240, 250, 340, or 350. Similarly, the sensor 560 may be the same as or substantially similar to any one of the sensors 250 or 350.

Figure 5H:
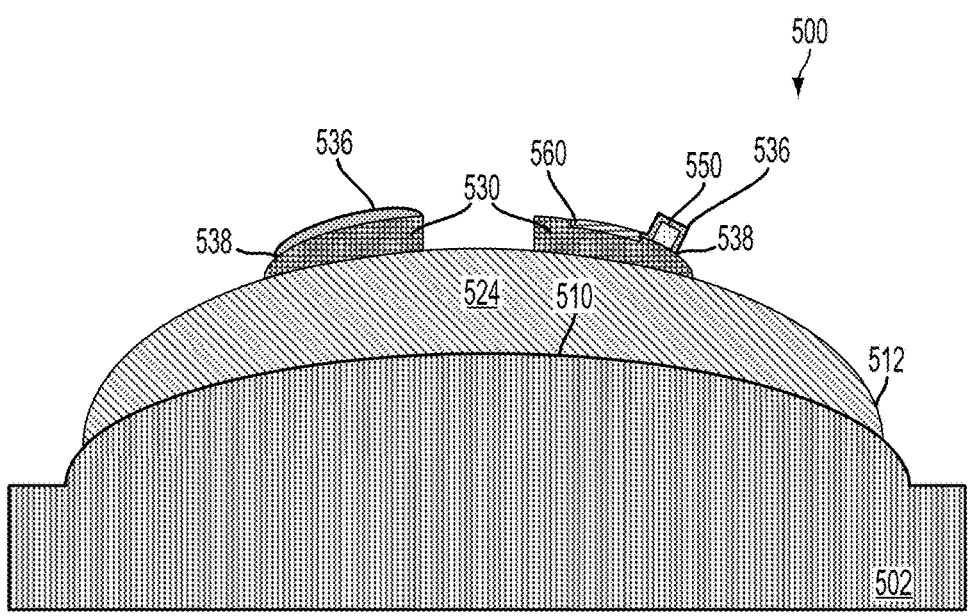

In other examples, however, the dyed polymer layer 536 may cover the electronic device 550. FIG. 5h shows one such example. In the illustrated example, the second portion 538 of the electronic structure 530 may include the electronic device 550. Consequently, the dyed polymer layer 536 may cover the electronic structure 550. Moreover, in examples in which the second portion 538 includes substantially all anterior surfaces of the electronic structure 530, the dyed polymer layer 536 may cover substantially all of the anterior surfaces of the electronic structure 530, for example, except for sensor 560 (in some examples, even sensor 560 may be covered).

Figure 5I:
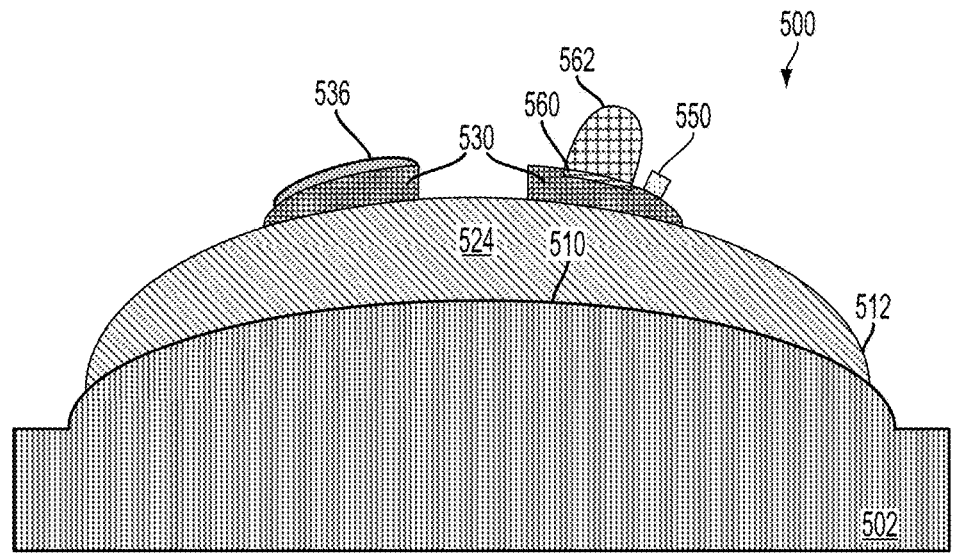

Continuing from the example of FIG. 5g, FIG. 5i shows a cross-sectional view of the fabrication device 500 in which a mask layer 562 is formed over the sensor 560. The mask layer 562 may be formed over the sensor 560 in a variety of ways. In an example, the mask layer 562 can be formed over the sensor 560 by placing one or more drops of a forming solution over the sensor 560. The forming solution may then be dried to form the mask layer 562.

In one example, the one or more drops of the forming solution can be placed over the sensor 560 based on the predetermined rotational orientation by a positioning apparatus or other suitable component of the fabrication device 500. Other techniques for placing the one or more drops of the forming solution over the sensor 560 based on the predetermined rotational orientation are possible as well.

In one example, the forming solution can comprise water and a water-soluble material, such as polyethylene glycol. Other forming solutions are possible as well.

Figure 5J:
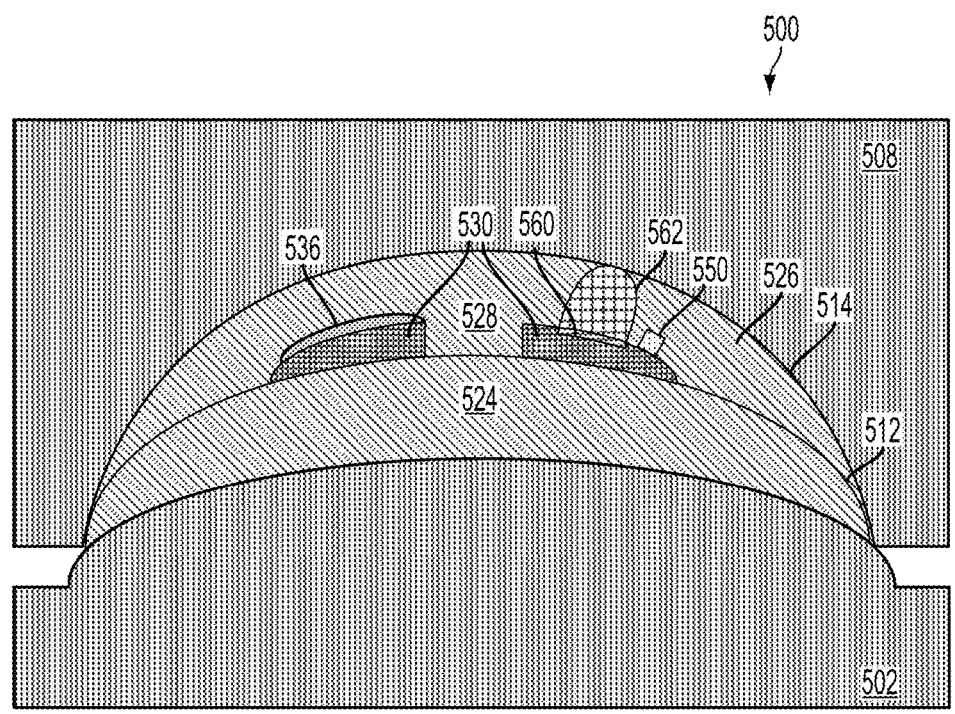

FIG. 5j shows a cross-sectional view of the fabrication device 500 in which a fourth molding piece 508 is used to provide a second polymer layer 528. The first molding piece 502 and the fourth molding piece 508 may define a second cavity.

The fabrication device 500 may provide a polymer material 526 over the first polymer layer 524, the electronic structure 530, and the dyed polymer layer 536. In one example, the polymer material 526 is the same as or is substantially similar to the polymer material 522 used to form the first polymer layer 524. Moreover, the polymer material 526 may also include the same as or a substantially similar polymer material as the dyed polymer material 532 used to form the dyed polymer layer 536. In other examples, the polymer material 526 may include one or more polymer materials other than the polymer material 522 or the dyed polymer material 532. However, in examples in which the body-mountable device is an eye mountable device, as in FIG. 5j, the second polymer material 528 is transparent.

In one example, the fabrication device 500 may include or more alignment pins (not shown), such as one or more dowel pins, for aligning the fourth molding piece 508. Additionally or alternatively, the fabrication device 500 may include one or more other components or structures for mechanically aligning the fourth molding piece 508. In another example, the fabrication device 500 includes a robotic system (not shown) configured to align the fourth molding piece 508 over the first molding piece 502. In an additional or alternative example, the fabrication device 500 may include one or more additional components to align the fourth molding piece 508 over the first molding piece 502, such as, perhaps, a visual alignment system. Other examples may also be possible.

The polymer material 526 may be formed into a second polymer layer 528 by compression between the first molding piece 502 and the fourth molding piece 508. However, the mask layer 562 may block the second polymer layer 528 from forming over the sensor 260. As a result, the fabrication device 500 may form the second polymer layer 528 such that the dyed polymer layer 536 and the electronic structure 530 such are fully enclosed by the first polymer layer 524 and the second polymer layer 528 except for the sensor 560, which may be enclosed by the mask layer 562.

The first molding piece 502 and the fourth molding piece 508 may be configured to achieve a given desired thickness of a layer formed between the two pieces. As one example, the first molding piece 502 and the fourth molding piece 508 may be designed so as to define a thickness of the second polymer layer 528. As another example, the first molding piece 502 and the fourth molding piece 508 may be designed so as to define a final thickness of an eye-mountable device, such as the eye-mountable device 400. In an example, the first molding piece 502 and the fourth molding piece 508 may be designed so as to allow for a layer having a given desired thickness between the two pieces (in addition to a thickness of the first polymer layer 524). As such, when the first molding piece 502 and the fourth molding piece 508 are pressed together during formation of a layer, the resulting layer will have the given desired thickness.

In one example, the second polymer layer 528 has a thickness of greater than 50 micrometers. However, in other examples, the second polymer layer 528 may have a thickness between about 50 and about 300 micrometers, such as about 130 micrometers. It should be understood that since the second polymer layer 528 molds over the dyed polymer layer 536 and the electronic structure 530, the second polymer layer 528 may not have a uniform thickness. For instance, the thickness of the second polymer layer 528 above the dyed polymer layer 536 may be less than the thickness of the second polymer layer 528 that is not touching the sen dyed polymer layer 536.

In another example, the thickness of the second polymer layer 528 may be selected based on a particular analyte or analytes that the body-mountable device, such as example eye-mountable devices 300 or 400, is configured to detect. For example, an optimal thickness for a first analyte may be about 10 micrometers, while an optimal thickness for a second analyte may be about 25 micrometers. Other examples are possible as well.

The second polymer layer 528 may define an anterior side 514 of an eye-mountable device. That is, the second polymer layer 528 may define an outer edge of the eye-mountable device. When mounted on an eye of a user, the anterior side 514 may correspond to the side of the device that is not touching the eye of the user. The fourth molding piece 508 may be shaped so as to define a shape of the anterior side 514. In examples in which the second polymer layer 528 is a component of a contact lens, fourth molding piece 508 may shape the anterior side 514 to have a curvature of the second cavity based on, perhaps, the user's contact lens prescription. That is, the curvature of the anterior side 514 may provide a given amount of visual correction when the eye-mountable device is worn.

After the second polymer layer 528 is formed, the fabrication device 500 may cure the second polymer layer 528. The second polymer layer 528 can be cured by any of the techniques mentioned herein. In an example, the second polymer layer 528 can be cured like the first polymer layer 524 and/or the dyed polymer layer 536. However, in other examples, the second polymer layer 528 may be cured by different techniques than the either of the first polymer layer 524 or the dyed polymer layer 536. In yet another example, the fabrication device 500 may also cure or finish curing the first polymer layer 524 and/or the dyed polymer layer 536 at this stage.

Figure 5K:
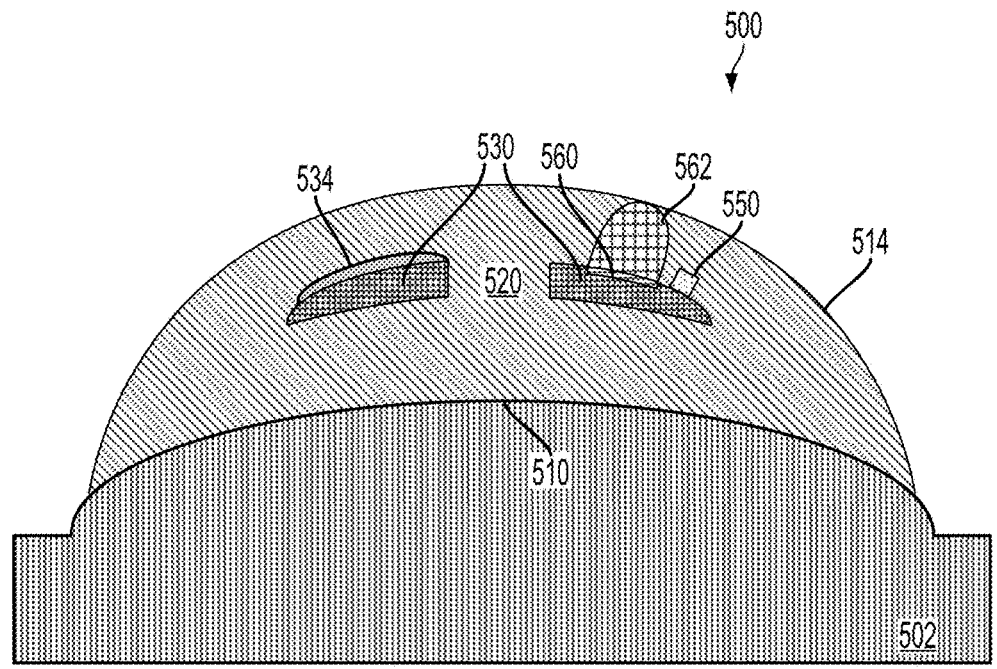

After the second polymer layer 528 is cured, the fabrication device 500 may separate the fourth molding piece 508 from the first molding piece 502. At this point, there may not be a visible boundary line (e.g., the upper surface 512) separating the first polymer layer 524 from the second polymer layer 528. That is, the first polymer layer 524 and the second polymer layer 528 may appear as a transparent polymer 520, as shown in FIG. 5*k*. The transparent polymer 520 may be the same as or substantially similar to the transparent polymer 320.

Figure 5L:
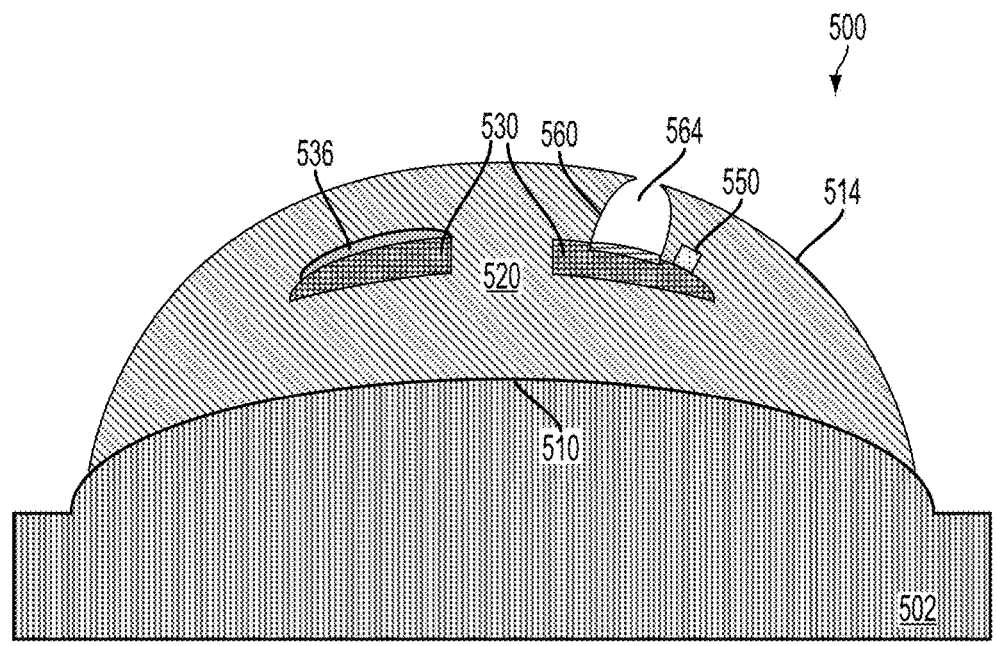

FIG. 5*l* shows a cross-sectional view of the molding apparatus 500 in which the mask layer 562 is dissolved, thereby providing a channel 564 in the transparent polymer 520 over the sensor 560.

The mask layer 562 can be removed to form the channel 564 in a variety of ways. As one example, the mask layer 502 can be removed to form the channel 564 by dissolving the mask layer 502. In an example, the mask layer 562 can be dissolved by soaking each of the mask layer 564 and the transparent polymer 520 in a dissolving fluid that dissolves the mask layer 562. The dissolving fluid may be selected based on the forming solution, the first polymer material 522, and/or the polymer material 526. With this arrangement, the dissolving fluid may not dissolve the transparent polymer 520. Other techniques for dissolving the mask layer 562 are possible as well.

After the mask layer 562 is released, a body-mountable device may be completed, and the fabrication device 500 may be configured to remove the body-mountable device from the first molding piece 502 using any suitable process, method, or technique.

Figure 6:
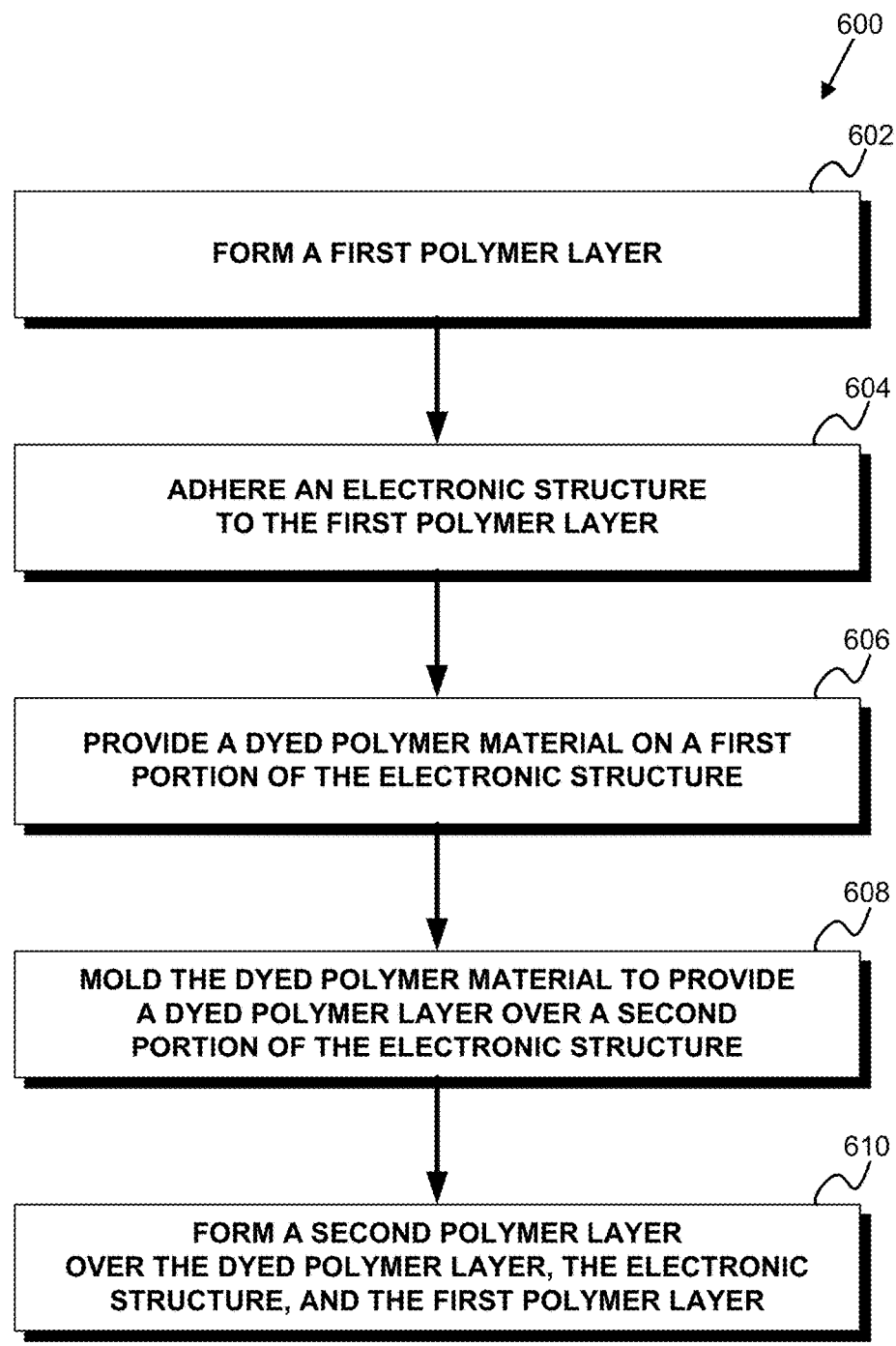
FIG. 6 is a flow chart illustrating a method, according to an example embodiment.

FIG. 6 is a flow chart illustrating a method, according to an example embodiment. The method 600 is one example of a method that may be implemented to fabricate a body-mountable device, such as one of the eye-mountable devices described with respect to FIGS. 1-4*b*. For purposes of illustration, the method 600 is described below as being carried out by a molding apparatus that utilizes cast or compression molding. It should be understood, however, that the method 600 may be carried out by a molding apparatus that utilizes other methods for forming the polymer layers. It should also be understood that the method 600 may be carried out by more than one molding apparatus.

Moreover, for purposes of illustration, the method 600 is described below in a scenario where a body-mountable device is an eye-mountable device. It should be understood, however, that the method 600 may involve scenarios where the body-mountable device comprises other mountable devices that are mounted on or in other portions of the human body. For example, the method 600 may involve scenarios where the body-mountable device comprises a tooth-mountable device and/or a skin-mountable device as described herein. Further, while reference is made to components of the electronic structure 230 described with respect to FIGS. 2*a*-2*b* and the eye-mountable devices 300 and 400 described with respect to FIGS. 3*a*-3*d* and 4*a*-4*d*, respectively, it is understood that other components and/or devices may also be used.

At block 602, the method 600 comprises forming a first polymer layer. Performing block 602 may provide a first polymer layer that is the same as or is substantially similar to the first polymer layer 524 described with respect to FIG. 5*a*. The molding apparatus may perform functions that are the same as or are substantially similar to the functions of the fabrication device 500 described with respect to FIG. 5*a*.

At block 604, the method 600 comprises adhering an electronic structure to the first polymer layer. The electronic structure may be the same as or substantially similar to one of the electronic structures 230 or 330. Other electronic structures are possible as well. The molding apparatus, when performing the steps of block 604, may perform functions that are the same as or are substantially similar to the functions of the fabrication device 500 described with respect to FIG. 5*b*.

At block 606, the method 600 includes providing a dyed polymer material on a first portion of the electronic structure. The dyed polymer material may be the same as or substantially similar to the dyed polymer material 532 described with respect to FIG. 5*c*. Moreover, the molding apparatus, when performing the steps of block 606, may perform functions that are the same as or are substantially similar to the functions of the fabrication device 500 described with respect to FIG. 5*c*.

At block 608, the method 600 includes molding the dyed polymer material to provide a dyed polymer layer over a second portion of the electronic structure. The dyed polymer layer may be the same as or substantially similar to one of the dyed polymer layers 436 or 536. Additionally, the molding apparatus, when performing the steps of block 608, may perform functions that are the same as or are substantially similar to the functions of the fabrication device 500 described with respect to one or more of FIGS. 5d-5h.

At block 610, the method 600 includes forming a second polymer layer over the dyed polymer layer, the electronic structure, and the first polymer layer. The second polymer layer may be the same as or substantially similar to the second polymer layer 528 described with respect to FIG. 5j. Further, the molding apparatus, when performing the steps of block 610, may perform functions that are the same as or are substantially similar to the functions of the fabrication device 500 described with respect to one or more of FIGS. 5i-5l.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A method comprising:
    forming a first polymer layer;
    adhering an electronic structure to the first polymer layer, wherein the electronic structure comprises at least one antenna, a sensor, and an electronic device;
    providing a dyed polymer material on the electronic structure;
    molding the dyed polymer material to provide a dyed polymer layer that covers a portion of the electronic structure, wherein the dyed polymer layer reduces a visibility of one or more components of the electronic structure included in the portion of the electronic structure; and
    forming a second polymer layer over the dyed polymer layer, the electronic structure, and first polymer layer.

2. The method of claim 1, wherein the dyed polymer layer covers substantially all of a surface of the at least one antenna.

3. The method of claim 2, wherein the electronic structure comprises a posterior side and an anterior side, and wherein the portion of the electronic structure includes a surface on the anterior side of the electronic structure.

4. The method of claim 1, wherein dyed polymer layer covers substantially all of one or more surfaces of the electronic device.

5. The method of claim 1, wherein the first polymer layer defines a posterior surface of an eye-mountable device and the second polymer layer defines an anterior surface of the eye-mountable device.

6. The method of claim 1, wherein a color of the dyed polymer layer comprises one or more shades of blue, hazel, green, brown, or black.

7. The method of claim 1, wherein molding the dyed polymer material comprises:
    aligning, over the electronic structure, a mold that has a shape substantially similar to at least the portion of the electronic structure; and
    using the mold to compress the dyed polymer material on a surface of the electronic structure.

8. The method of claim 7, wherein a cavity of the mold is configured to provide a thickness of the dyed polymer layer that is between about 10 micrometers and about 100 micrometers.

9. The method of claim 1, wherein the dyed polymer comprises silicone.

10. The method of claim 1, wherein the dyed polymer layer and at least one of the first polymer layer or the second polymer layer comprise a substantially similar polymer material.

11. The method of claim 1, wherein the dyed polymer layer is substantially opaque.

* * * * *